(12) United States Patent
Lippert et al.

(10) Patent No.: US 10,751,544 B2
(45) Date of Patent: Aug. 25, 2020

(54) OPTICAL STIMULATION DEVICE AND METHOD FOR PROGRAMMING

(71) Applicants: LEIBNIZ-INSTITUT FUER NEUROBIOLOGIE MAGDEBURG, Magdeburg (DE); OTTO-VON-GUERICKE-UNIVERSITAET MAGDEBURG, Magdeburg (DE); OTTO-VON-GUERICKE-UNIVERSITAET MEDIZINISCHE FAKULTAET, Magdeburg (DE)

(72) Inventors: Michael Lippert, Leipzig (DE); Frank Ohl, Osterweddingen (DE); Kathrin Janitzki, Magdeburg (DE); Hans-Joachim Heinze, Magdeburg (DE)

(73) Assignees: LEIBNIZ-INSTITUT FUER NEUROBIOLOGIE MAGDEBURG, Magdeburg (DE); OTTO-VON-GUERICKE-UNIVERSITAET MAGDEBURG, Magdeburg (DE); OTTO-VON-GUERICKE-UNIVERSITAET MEDIZINISCHE FAKULTAET, Magdeburg (DE)

(*) Notice: Subject to any disclaimer, the term of this patent is extended or adjusted under 35 U.S.C. 154(b) by 859 days.

(21) Appl. No.: 15/313,334

(22) PCT Filed: May 22, 2015

(86) PCT No.: PCT/EP2015/061400
§ 371 (c)(1),
(2) Date: Nov. 22, 2016

(87) PCT Pub. No.: WO2015/177345
PCT Pub. Date: Nov. 26, 2015

(65) Prior Publication Data
US 2017/0189712 A1    Jul. 6, 2017

(30) Foreign Application Priority Data

May 23, 2014    (DE) .................. 10 2014 107 298

(51) Int. Cl.
A61N 5/06         (2006.01)
A61B 18/00        (2006.01)
A61N 5/067        (2006.01)

(52) U.S. Cl.
CPC ......... *A61N 5/0622* (2013.01); *A61N 5/0601* (2013.01); *A61B 2018/00839* (2013.01);
(Continued)

(58) Field of Classification Search
CPC ............... A61N 5/0622; A61N 5/0601; A61N 2005/067; A61N 2005/0651;
(Continued)

(56) References Cited

U.S. PATENT DOCUMENTS

2006/0173259 A1 *  8/2006  Flaherty ............... A61B 5/0031
                                                600/331
2008/0051882 A1 *  2/2008  Rubin .................. A61L 29/148
                                                623/1.42

(Continued)

FOREIGN PATENT DOCUMENTS

DE    10 2012 110 358 A1    10/2012
DE    10 2012 002 663 A1    8/2013
(Continued)

OTHER PUBLICATIONS

Zhang et al, "Integrated device for optical stimulation and spatiotemporal electrical recording of neural activity in light-sensitized brain tissue", Journal of Neural Engineering, Sep. 1, 2009, p. 55007, vol. 6, No. 5, Institute of Physics Publishing, Bristol, GB.

*Primary Examiner* — Gary Jackson
*Assistant Examiner* — Sebastian X Lukjan
(74) *Attorney, Agent, or Firm* — W&C IP (57) ABSTRACT

The invention relates to an optical stimulation device for stimulating nerve cells, wherein the stimulation device has at least one implant component, which is designed for
(Continued)

implanting in a natural inner cavity of the body of a living being, through which cavity a bodily fluid flows, having the following features: a) the implant component has at least one supporting structure, which can be expanded in a radial direction for fastening in the natural inner cavity, b) a plurality of light sources is fastened to the supporting structure, which light sources are designed to emit light in the radial direction with respect to the supporting structure, c) a plurality or electrodes is fastened to the supporting structure, which electrodes are designed to capture electrical body signals, d) the supporting structure has a plurality of openings and/or channels, through which the bodily fluid can flow after implantation in the body. The invention further relates to a method for programming the parameter memory of a stimulation device.

14 Claims, 6 Drawing Sheets

(52) U.S. Cl.
CPC .............. *A61N 2005/067* (2013.01); *A61N 2005/0612* (2013.01); *A61N 2005/0626* (2013.01); *A61N 2005/0629* (2013.01); *A61N 2005/0651* (2013.01); *A61N 2005/0652* (2013.01)

(58) Field of Classification Search
CPC .... A61N 2005/0626; A61N 2005/0612; A61N 2005/0652; A61B 2018/00839
See application file for complete search history.

(56) References Cited

U.S. PATENT DOCUMENTS

| | | |
|---|---|---|
| 2008/0281305 A1 | 11/2008 | Baynham et al. |
| 2009/0088449 A1* | 4/2009 | Barlow ................ A61K 31/439 514/291 |
| 2009/0112278 A1* | 4/2009 | Wingeier ............. A61B 5/6864 607/45 |
| 2010/0145415 A1 | 6/2010 | Dahm et al. |
| 2011/0295331 A1 | 12/2011 | Wells et al. |
| 2011/0295347 A1* | 12/2011 | Wells ................... A61N 5/0601 607/89 |
| 2012/0165759 A1* | 6/2012 | Rogers ................ A61B 5/6867 604/264 |
| 2012/0253261 A1* | 10/2012 | Poletto .............. A61M 5/14276 604/20 |
| 2013/0030353 A1* | 1/2013 | Seymour .............. A61N 5/0622 604/20 |
| 2013/0046148 A1 | 2/2013 | Tathireddy et al. |

FOREIGN PATENT DOCUMENTS

| | | | | |
|---|---|---|---|---|
| WO | WO-2013136337 A1 * | 9/2013 | ........... | A61B 5/6853 |
| WO | WO-2014169190 A1 * | 10/2014 | ........... | A61N 5/0622 |
| WO | WO-2014179331 A2 * | 11/2014 | ............. | C12N 15/85 |

* cited by examiner

OPTICAL STIMULATION DEVICE AND METHOD FOR PROGRAMMING

CROSS-REFERENCE TO RELATED APPLICATIONS

This application is a national stage application of International Application PCT/EP2015/061400 filed May 22, 2015 and claims benefit of German patent application 102014107298.7, filed May 23, 2014.

FIELD OF THE INVENTION

The invention relates to an optical stimulation device for stimulating nerve cells as claimed in claim 1. The invention also relates to a method for programming the parameter memory of a stimulation device as claimed in claim 10.

BACKGROUND OF THE INVENTION

In general, the invention relates to the field of optical stimulation of nerve cells, i.e., of stimulation by light. The invention thus relates to the field of optogenetics. The development of optogenetics, of the sensitization of normal nerve cells to light by genetic techniques, nurtures the hope of being able to use light to treat a range of diseases by temporally and spatially selective activation or inhibition of neuronal structures. Current systems are based on the stereotactic placement of electrodes and light sources directly in brain tissue or on the surface of the brain. This is associated with complicated surgical procedures and corresponding risks. Furthermore, the necessary stereotactic planning complicates broad applicability.

Moreover, the implantation of the light-generating structures leads to a not negligible heat input in the brain. To avoid brain damage, the possible attainable output density of the light signals is greatly limited.

SUMMARY OF THE INVENTION

It is therefore an object of the invention to specify an optical stimulation device for stimulating nerve cells, which device has a higher efficiency together with simplified applicability and thereby opens the way to a broader applicability of optogenetic treatment methods.

This object is achieved as claimed in claim 1 by an optical stimulation device for stimulating nerve cells, the stimulation device having at least one implant component configured for implantation in a natural inner cavity of the body of a living organism, through which cavity a body fluid flows, having the following features:

a) the implant component has at least one support structure which is expandable in the radial direction for fixation in the natural inner cavity, b) attached to the support structure is a multiplicity of light sources which are configured for radiation of light in the radial direction with respect to the support structure, c) attached to the support structure is a multiplicity of electrodes which are configured for capturing electric body signals, d) the support structure has multiple openings and/or channels through which the body fluid can flow after implantation in the body.

The invention has the advantage that, for the first time, it is possible to specify an optical stimulation device for stimulating nerve cells, more particularly nerve cells of the brain, which can be deployed by noninvasive or minimally invasive surgical techniques. More particularly, the implant component can be placed endoscopically in the desired inner cavity of the body and anchored there by effecting a fixation in the natural inner cavity by expansion of the support structure in the radial direction. The fixation can, for example, be effected by balloon expansion, as known from stents. To fit and place the implant component in the inner cavity, it is, for example, possible to use a flexible guide rod, for example in the form of a catheter. Advantageously, it is, for example, possible to use a ventricle space for the placement of the implant component. In this case, the insertion of the implant component into the ventricle space is performable in a noninvasive manner, by the wall of the ventricle not being broken through, but by the placement of the implant component taking place via the openings of the ventricle system. A minimally invasive placement is possible too when there is a piercing of a brain structure which leads to fewest possible adverse effects. Moreover, the minimally invasive or noninvasive nature of the stimulation device according to the invention allows its exchange in the event of a defect or a further development of the stimulation device. A repositioning is possible too without additional damage occurring in the brain tissue.

The open structure of the support structure, i.e., the openings and/or channels, allows a flow through the support structure and thus the implant component after implantation in the body by means of body fluid, making it possible for a cooling of the light sources to take place in a natural manner. In this way, it is possible to resolve the heat problem due to the light sources that was mentioned at the beginning. In the case of placement of the implant component in the ventricle space, as mentioned, the cerebrospinal fluid can be directly used to cool the light sources. As a result, an especially efficient cooling is possible, enabling considerably higher radiatable light outputs. At the same time, brain tissue damage due to unallowable heating can be avoided.

Owing to the radiation of light in the radial direction with respect to the support structure, the light is directly emitted into the surrounding tissue. In this connection, the radiation of light need not exclusively take place exactly in the radial direction. To achieve a high optical efficiency, it is advantageous when the radial component of the direction of light radiation is the predominant component.

By means of the optical stimulation device according to the invention, a treatment of the following diseases is possible:

Stimulation of the locus coeruleus:

Neurodegenerative diseases such as Parkinson's disease and Alzheimer's disease, which are characterized by an early degeneration of the LC, Severe psychiatric symptoms, such as major depression, Korsakoff's syndrome, anxiety disorders, PTSD, which are characterized by altered discharges of the LC, Disorders of wakefulness/locked-in syndrome through stimulation of the locus coeruleus or of the ARAS, In the case of narcolepsy or after unilateral cerebral infarction or bleeding in the brainstem region, Disorders of autonomous control loops through stimulation/inhibition of the hypothalamus, Eating disorders, hyperactivation of the HPA axis in the course of many diseases, therapy-resistant hypertonia, Addictions and psychoses through indirect stimulation of frontal cortex areas via activation of ascending monoaminergic pathways (e.g., of the medial forebrain bundle, which stretches from the VTA and the LC to the nucleus accumbens), Neurodegenerative diseases/memory disorders through an influence on the hippocampus (placement of the implant component in the inferior horn of the lateral ventricle)

Even in the absence of a genetic influence, it is possible to advantageously use the optical stimulation device according to the invention. This is possible owing to the presence of endogenous light-sensitive nerve cells in the brain of vertebrates. In addition, it is possible to utilize thermal effects of infrared light for the focal heating of certain brain structures in order to modulate the activity thereof. Likewise possible is a utilization of the suppression of neuronal activity by means of the bleaching properties of blue and green light on the flavoproteins of the respiratory chain.

By means of a direct light stimulation without added optogenetic proteins, a treatment of therapy-resistant severe depressions, for example, appears possible.

According to an advantageous development of the invention, the implant component has a control electronics system or is connected via lines to a control electronics system arranged distantly from the implant component, the control electronics system being configured for signal conditioning and/or signal processing of the signals received via the electrodes and/or for activating the light sources. The control electronics system can be designed as one piece or as multiple pieces, for example in the form of a headstage electronics system directly arranged on or at the implant component and of a distantly arranged main electronics system which is connected via lines to the implant component and especially the headstage electronics system thereof. In this way, the necessary electronics system can, as far as necessary, be directly arranged at the implant component, for example in order to allow an immediate signal conditioning of the signals of the electrodes. As a result, the headstage electronics system can be kept small in terms of structure. Further necessary components can then be accommodated in the main electronics system.

The light sources can be electric light sources, for example in the form of semiconductor light sources, especially in the form of light-emitting diodes (LED) or laser diodes. The light sources can also be passive light sources, for example in the form of light-emitting surfaces of optical waveguides or prisms arranged at optical waveguides, micromirrors or other optics. In the case of passive light sources, the lines leading to the light sources can be especially optical waveguides, for example in the form of glass fibers. This has the advantage that the optical stimulation device is MRI-compatible, i.e., does not interfere with the recordings by means of a magnetic resonance (MRI) scanner. If the light sources used are electric light sources arranged at or in the implant component, the lines used are electric conductors (cables). The light sources attached to the support structure can also be a combination of electric light sources and passive light sources.

According to an advantageous development of the invention, the light sources are attached to the support structure in a predefined position with respect to the electrodes.

According to an advantageous development of the invention, the control electronics system has a parameter memory in which an item of information is stored for each light source, regarding whether the light source is activatable or not for the purposes of stimulation. This has the advantage that the placement of the implant component in the inner cavity of the body is simplified, since an especially high precision of positioning is not required. Instead, the implant component can be "overloaded", so to speak, with the light sources, i.e., can have more light sources than is necessary for the actual nerve stimulation. Owing to the known position of the light sources with respect to the electrodes at the support structure, it is possible, by means of trial-based activation of individual light sources and receiving of the electrode signals, to test which light sources are most favorably oriented with respect to the nerve cells. For said light sources, it is then possible to store in the parameter memory the item of information that the light source is activatable for the purposes of stimulation. For the remaining light sources, it is possible to store the item of information that it is not activatable for the purposes of stimulation and accordingly remains switched off in later operation of the optical stimulation device. As a result, the electric activation and thus the associated heat input are limited to what is necessary. There is no unnecessary activation of light sources which have no influence or no substantial influence on the nerve cells.

The identification of the activatable light sources can be carried out by measurement via the electrodes themselves or by means of a response measured in another way, for example by EEG, behavioral response, functional magnetic resonance imaging, PET, SPECT, pharmacological methods. If the identification of the activatable light sources is not carried out by measurement via the electrodes, it is not absolutely necessary to arrange the light sources at the support structure in a predefined position with respect to the electrodes.

According to an advantageous development of the invention, the support structure has, in the nonexpanded state, a circumference of less than 10 mm, more particularly less than 6 mm. This has the advantage that a minimally invasive or noninvasive placement of the implant component is possible in virtually any body of a living organism.

According to an advantageous development of the invention, the support structure comprises a material having a high thermal conductivity. More particularly, the thermal conductivity is greater than 10 W/m·K. This has the advantage that the support structure additionally contributes to cooling by better transfer of the heat arising at the light sources to the body fluid which serves as coolant and which is situated in the inner cavity together with the implant component.

According to an advantageous development of the invention, one, multiple or all light sources have thermally conductive heat sinks. As a result, the dissipation of heat from the light sources is further improved.

According to an advantageous development of the invention, the implant component has a coupling element via which the implant component is coupleable to a flexible guide rod to be coupled to the implant component for carrying out the implantation process, the coupling of the coupling element to the flexible guide rod being disengageable by actuation of a release mechanism. This is additionally beneficial for a minimally invasive or noninvasive placement of the implant component in the inner cavity of the body. The flexible guide rod can, for example, be designed as an endoscope or a catheter. By means of the release mechanism, which can, for example, be remotely operable from a handle of the flexible guide rod, it is possible, after correct placement of the implant component in the inner cavity of the body, to disengage the guide rod therefrom and to remove it from the body. Beforehand, it is possible, via an expansion mechanism which is likewise triggerable via the flexible guide rod, to expand the support structure in order to fix the implant component in the inner cavity of the body.

According to an advantageous development of the invention, some or all light sources are individually activatable.

This has the advantage that, through targeted activation of certain light sources, it is possible to realize special treatment methods which would not be possible in the case of simultaneous activation of all light sources. As a result, the application range of the optical stimulation device is further improved.

According to an advantageous development of the invention, the light sources and/or the electrodes are attached on a flexible support material which is attached to the support structure. The flexible support material can, for example, be a silicone tube or a MEMS structure. In this connection, the flexible support material is formed with openings and/or channels at least to the extent that the desired through-flow of the body fluid is ensured. As a result, the producibility of the optical stimulation device is improved. For instance, the light sources, for example in the form of light-emitting diodes or laser diodes, can be printed onto a film or a silicone material and/or be strung onto the support structure in a thread-like manner, similar to a string.

As claimed in claim 10, the invention further provides a method for programming the parameter memory of a stimulation device of the abovementioned type, wherein all light sources for light emission are actuated first of all, the signals subsequently captured by means of the electrodes are evaluated or signals captured by other nerve-signal capture methods are evaluated, light sources from the total of the light sources present that will be activatable in future are determined therefrom, and the identification "activatable" is stored in the parameter memory for these light sources and the identification "nonactivatable" is stored for all other light sources. Using this method, the precise placement and adjustment of the implant component in the inner cavity of the body is simplified, since only an approximate placement in relation to the stimulatory nerve cells is initially necessary. By means of the described programming of the parameter memory, the light sources of the implant component which have a functional effect on the stimulation of the nerve cells are then detected. The other light sources are then not required from then on and can be designated as "nonactivatable". A further fine mechanical placement of the implant component is then not required.

In jurisdictions in which medical procedures are not excluded from patent protection, the invention further provides a method for implanting an optical stimulation device in a body of a human or animal, wherein an implant component of the optical stimulation device is placed endoscopically in a ventricle space of the body and fixed therein. Here, it is possible to use in particular an implant component of an optical stimulation device of the above-described type. As a result, it is possible to realize the abovementioned advantages.

According to an advantageous development of the invention, the implant component is fixed in the ventricle space by expanding a support structure of the implant component.

The following procedure, executed using the example of target structures close to aqueducts, is proposed for the endoscopic placement of the catheter: As in the endoscopic stenting of an aqueduct stenosis, a small trepanation (1.5 to 2 cm in diameter) is first performed approx. 2 to 4 cm anterior to the coronal suture and 2 cm right of the midline. Thereafter, the anterior horn of the right lateral ventricle is reached via a rigid or flexible neuroendoscope and, lastly, a French Fogarty balloon catheter is introduced into the aqueduct via the interventricular foramen and the third ventricle. The exact placement of the light-emitting tip of the catheter, in relation to the target structure, is done in accordance with a distance to a fixed point in the aqueduct that was previously precisely determined tomographically. The catheter is fixed via the expansion of the balloon in the aqueduct. It is thus possible to reach target structures in the vicinity of the fourth ventricle, especially the locus coeruleus. Navigation can be trained beforehand by means of software.

Another possible path to the fourth ventricle is from the occipital side via the natural openings to the subarachnoid space. The fourth ventricle is connected to the cisterna magna via the median aperture and on both sides to the cisterna pontis via the lateral aperture. Positioning and anchoring are done similarly to the above-described manner.

The invention will be more particularly elucidated below on the basis of exemplary embodiments with use of drawings.

Figure 1:
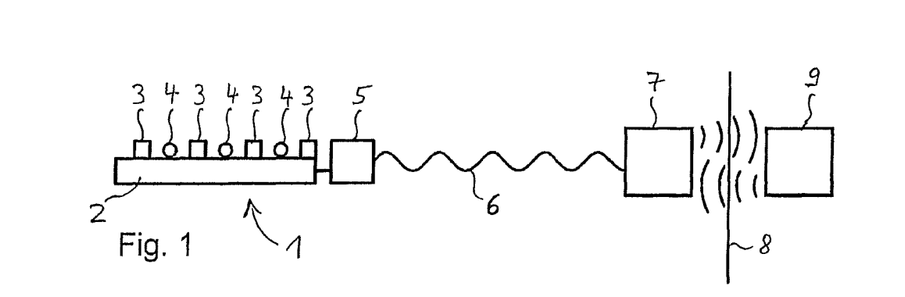
FIG. 1. Example of a general system structure of the optical stimulation device.

FIG. 1 shows an example of a general system structure of the optical stimulation device. What can be seen is a support structure 2 which is designed as a stent or catheter for example and to which light sources 3 and surface electrodes 4 are attached. As a result, an implant component 1 is provided. The implant component 1 has a headstage electronics system 5 which is directly connected thereto and which performs a signal conditioning and processing for ingoing and outgoing signals, for example impedance conversion, amplification, digitization, activation of the light sources. Here, light sources 3, for example in the form of LEDs, can be directly arranged on the support structure 2, or in the form of laser diodes in the headstage electronics system 5. The light thereof is then led out via optical waveguides to the positions depicted in the figure with the light sources 3.

The headstage electronics system 5 is connected via lines 6 to a main electronics system 7 of the system.

The main electronics system 7 undertakes data communication with external instruments 9 through the skin 8 and supplies power for the operation of the light sources and of the headstage electronics system 5. The main electronics system 7 can likewise carry out the interpretation of the signals and a possible feedback to the light sources and also store and evaluate data internally. If laser diodes are used, they can also be arranged in the main electronics system and be connected via optical waveguides to the implant component 1.

The headstage electronics system 5 and the main electronics system 7 form together a control electronics system of the stimulation device. This has a parameter memory in which a storage space, for example in the form of a bit or byte, is provided for each light source 3. In said storage space, it is possible to individually store for each light source an item of information regarding whether the light source is activatable or not for the purposes of stimulation.

Figure 2:
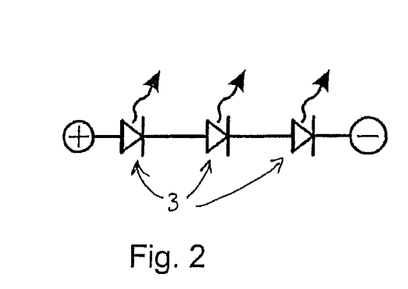
FIG. 2. Diagram of light sources or the laser diodes thereof connected in series.

As can be seen in FIG. 2, the light sources 3 or the laser diodes thereof can be connected in series, and this has the advantage that wiring is simpler and fewer lines are required.

Figure 3:
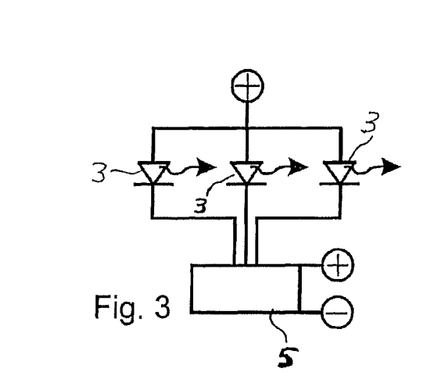
FIG. 3. Diagram of the light sources or the laser diodes thereof individually controlled by the headstage electronics system and/or main electronics system.

As can be seen in FIG. 3, the light sources 3 or the laser diodes thereof can also be individually controlled by the headstage electronics system 5 and/or main electronics system 7. This has the advantage that stimulation can be limited to a certain region by only some of the light sources present being activated.

Figure 4:
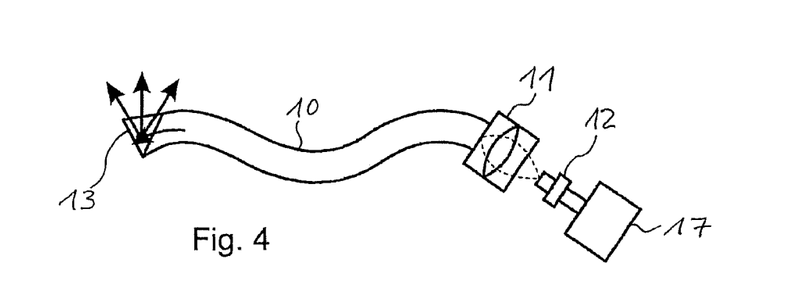
FIG. 4. Diagram of system structure when using optical waveguides.

FIG. 4 shows the system structure when using optical waveguides. The light source provided is an optical component 13 which is arranged at the end of an optical waveguide 10. The optical component 13 can, for example, be a micromirror, a prism or a similar optical component changing the direction of radiation. The optical component 13 reflects the light at an angle into the body tissue, which light is provided by a laser emitter 12 through the optical waveguide 10 and optionally an optics system 11 arranged at the optical waveguide 10 on the input side. For the activation of the laser emitter 12, a driver electronics system 17 is provided, which can, for example, be part of the main electronics system 7. Owing to the use of optical waveguides, the optical stimulation device is improved especially with respect to MRI compatibility.

Figure 5:
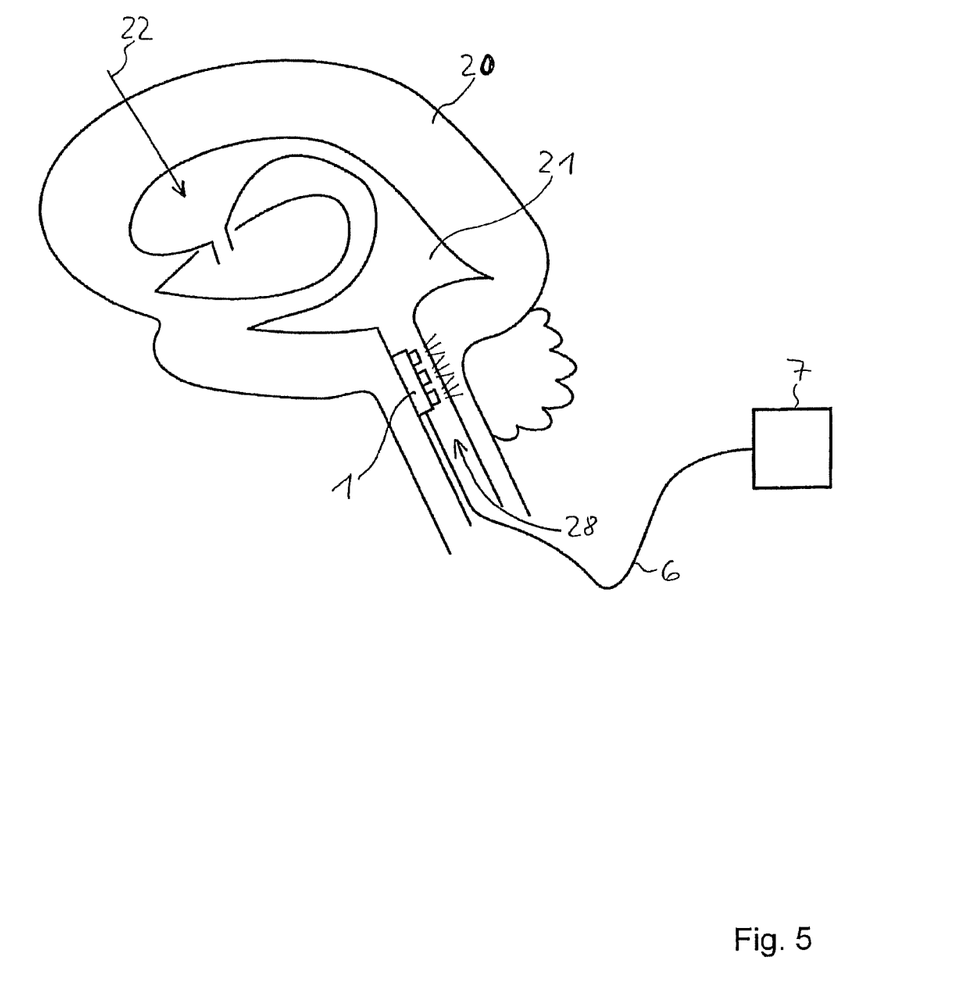
FIG. 5. Diagram of the structure and the anchoring of the optical stimulation device in the head of a human.

FIG. 5 shows the structure and the anchoring of the optical stimulation device in the head of a human. The implant component 1 having the light sources 3 and the electrodes 4 is placed in a ventricle space 21 and the cerebrospinal fluid present therein can be washed around said implant component to cool the light sources. The implant component and especially the support structure thereof are sufficiently permeable to liquids in order not to elicit any stasis. The implant component is connected via the lines 6 to the main electronics system 7. The main electronics system 7 can be implanted beneath the skin at a suitable site of the body, especially at a site other than in the head. The implantation of the implant component 1 in the brain 20 can be done in a minimally invasive manner. The implant component 1 can, for example, be introduced via a path 22 through healthy tissue at a site at which adverse effects are barely to be expected. Likewise possible is an implantation via one of the natural openings of the ventricle system without damaging the brain 20, i.e., via the path 28 depicted.

Figure 6:
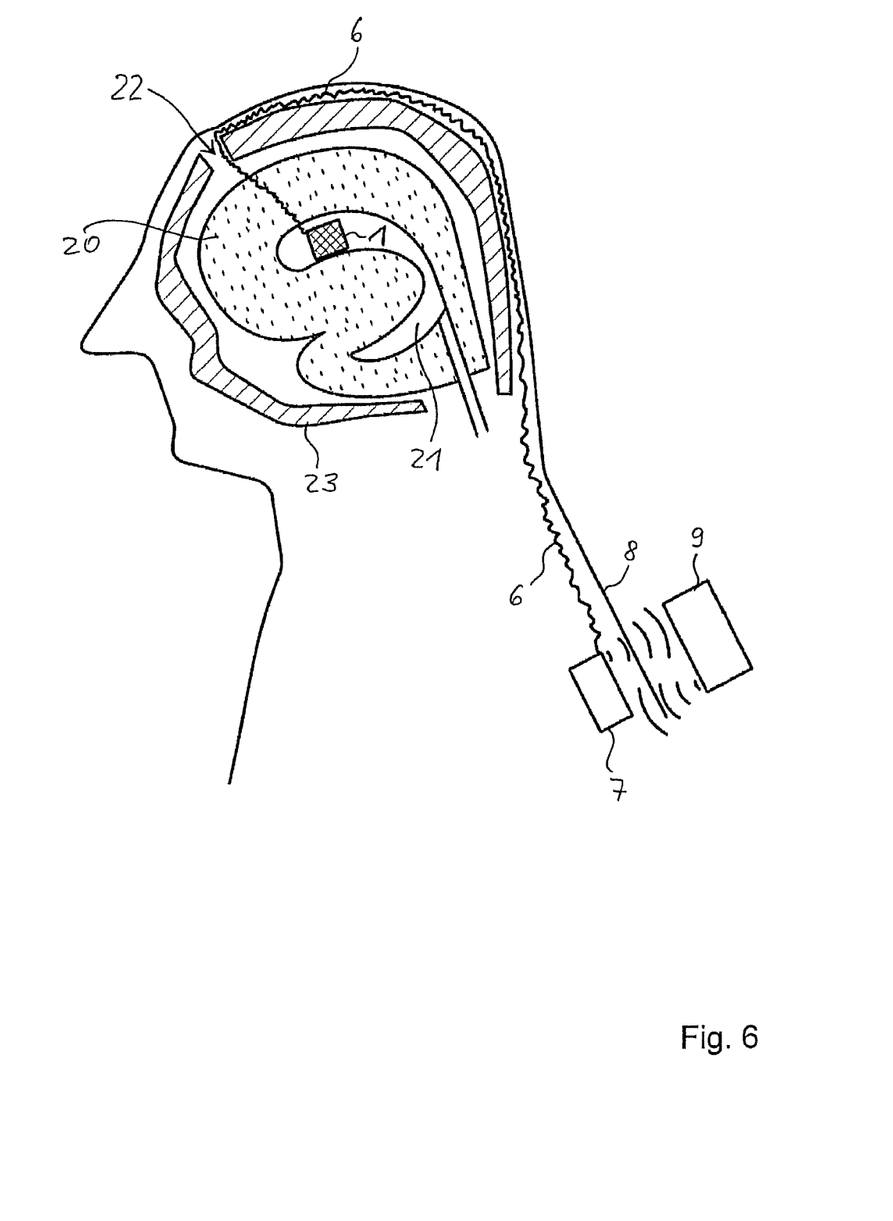
FIG. 6. Diagram of the placement of the implant component in the head.

FIG. 6 shows the placement of the implant component 1 in the head. The implant component 1 is situated in a ventricle space 21 of the brain 20. A connection for the lines 6 is ensured by a drilled hole 22 in the skull 23 or a natural skull opening to the outside. The main electronics system 7 is situated beneath the skin 8, not necessarily beneath the skin of the skull 23. The main electronics system 7 can communicate transdermally with external instruments 9.

Figure 7:
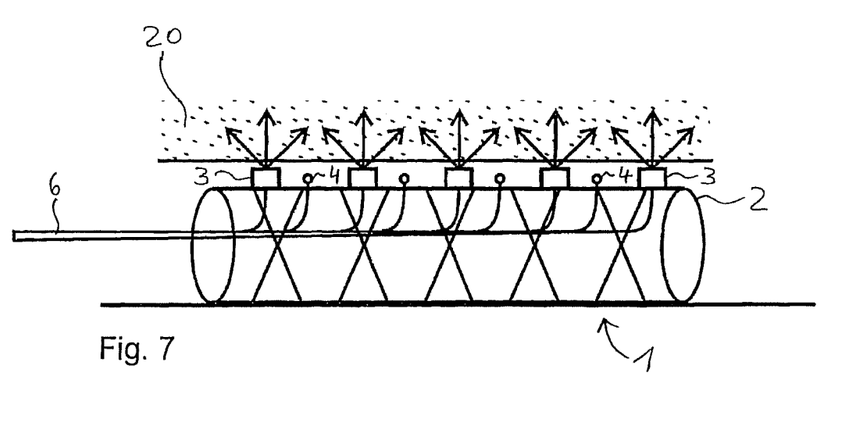
FIG. 7. An illustrative embodiment of the implant component.
Figure 15:
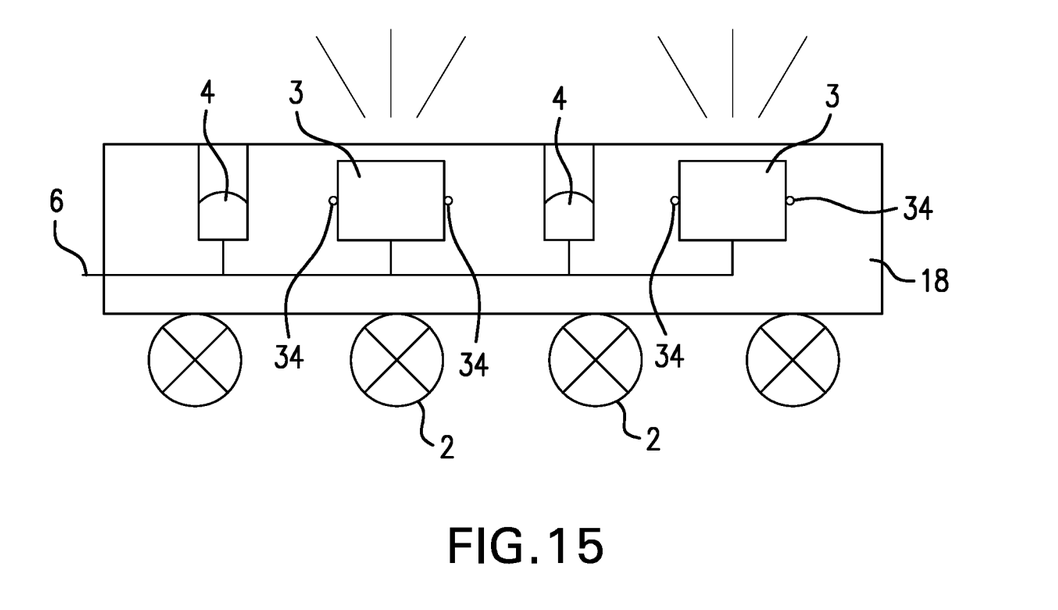
FIG. 15. Diagram of the light sources, channels/openings, the electrodes, and the lines incorporated into the thermally conductive flexible support material.

FIG. 7 shows, with further details, one embodiment of the implant component 1. A support structure 2 which is constructed with a lattice structure and which supports the light sources 3 and the electrodes 4 is placed in the ventricle space next to the brain 20. The support structure 2 is sufficiently permeable to cerebrospinal fluid by being formed with openings and/or channels 34 (see also FIG. 15). Situated on and/or in the support structure 2 are organic or crystalline semiconductor light sources 3 and surface electrodes 4 which are contacted by lines 6. The arrows indicate the radiation of light by the light sources 3 in the radial direction with respect to the support structure.

Figure 8:
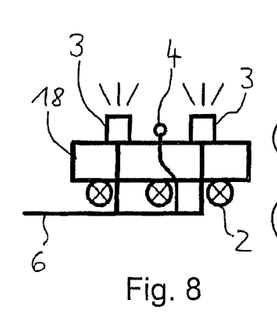
FIG. 8. Diagram of the light sources and electrodes applied on the surface of a flexible support material.
Figure 9:
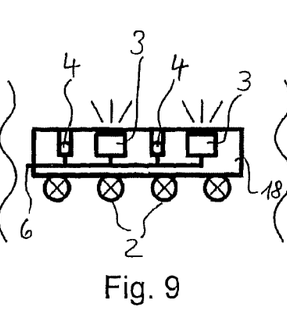
FIG. 9. Diagram of the light sources, the electrodes, and the lines incorporated into the thermally conductive flexible support material.
Figure 10:
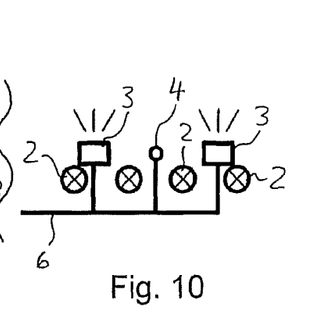
FIG. 10. Diagram of the electrodes and the light sources directly attached to the support structure.

FIGS. 8 to 10 show possible attachments of the light sources 3 and of the electrodes 4 to the support structure 2. FIG. 8 shows that the light sources 3 and electrodes 4 are applied on the surface of a flexible support material 18 which is additionally sufficiently thermally conductive, for example on a silicone material, for example in the form of a silicone tube, or on a MEMS structure. The support structure 2 is situated within the support material 18. The support structure 2 can, for example, be designed in the form of a stent, which structure allows an expansion to anchor the implant components in the inner cavity of the body. The lines 6 can run inside the support structure 2. Alternatively, the flexible support material 18 can also be arranged at the inner side of the support structure 2.

In FIG. 9, it can be seen that the light sources 3 and the electrodes 4 and also the lines 6 are incorporated into the thermally conductive flexible support material 18 in terms of thin-layer or thick-layer technology.

FIG. 10 shows that the electrodes 4 and the light sources 3 can be directly attached to the support structure 2 and accordingly participate in the change in shape (expansion).

Figure 11:
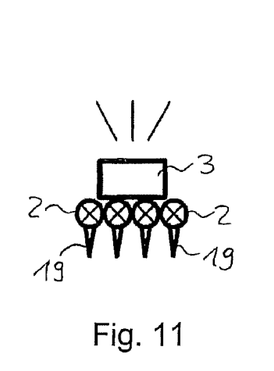
FIG. 11. Diagram of an option for the additional cooling of the light sources via the cerebrospinal fluid.

FIG. 11 shows one option for the additional cooling of the light sources via the cerebrospinal fluid. The light sources 3 can be equipped with small thermally conductive cooling structures (heat sink) 19 which deliver the heat which arises to the cerebrospinal fluid. Here, the material of the support structure 2 can additionally have a supportive effect if it is sufficiently heat-conductive.

Advantageously, the support structure 2 can, for example, be formed from one metallic material, similar to customary stents. As a result, heat dissipation can be further improved.

Figure 12:
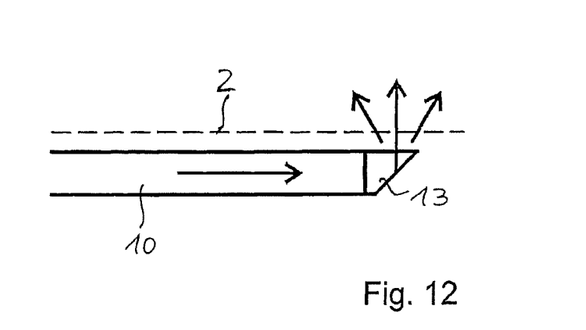
FIG. 12. Diagram of the use of optical fibers in conjunction with optical elements as light sources.

FIG. 12 shows the use of optical fibers (optical waveguides 10) in conjunction with optical elements 13 as light sources. To achieve MRI compatibility and, in addition, higher optical outputs, glass fibers can be used as optical waveguides 10. To guide the light to the surrounding tissue, such optical waveguides 10 are equipped at the end with optical elements 13 such as micromirrors or prisms, which bring about a deflection into the radial direction of light radiation. The light can then be radiated to the outside through the open support structure 2, i.e., in the radial direction with respect to the support structure.

Figure 13:
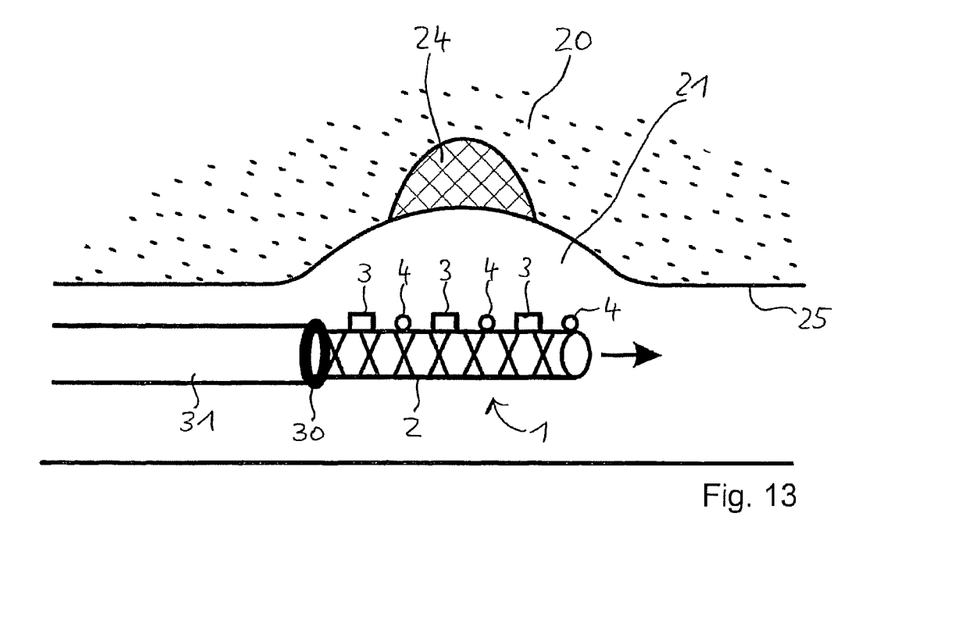
FIG. 13. Diagram of the insertion of the implant component by means of a flexible guide rod.

FIG. 13 shows the insertion of the implant component 1 by means of a flexible guide rod 31, for example an endoscope or a catheter. The guide rod 31 is mechanically coupled to a coupling element 30 of the implant component. Via a release mechanism which can be arranged at the flexible guide rod and/or at the implant component, this coupling can be undone in order to remove the guide rod 31 after placement of the implant component 1. This is done after expansion and corresponding anchoring of the implant component in the inner cavity, in this case in the ventricle space 21, as depicted in FIG. 14.

Figure 14:
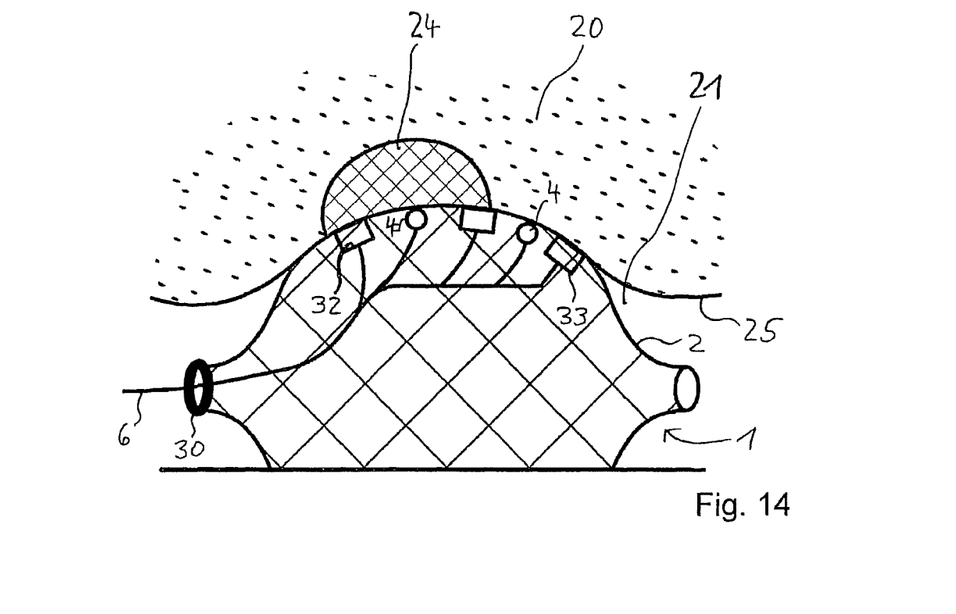
FIG. 14. Diagram of anchoring of the implant component in the ventricle space.

As can be additionally seen from FIG. 14, it is intended that the implant component be used to stimulate nerve cells 24. To this end, the implant component 1 is first approximately positioned within the brain 20 at the correct site by means of the guide rod 31. Thereafter, the support structure 2 is expanded, for example by means of balloon expansion. As a result, the light sources 3 and the electrodes 4 are pressed against the wall 25 of the ventricle space 21 without damaging said wall. The guide rod 31 is removed. What remains is the line 6 for connecting the implant component 1 to the main electronics system 7. A programming of the parameter memory of the stimulation device is then carried out such that, for example, the light source 32 is stored as "activatable" and the light source 33 as "nonactivatable". The nerve cells 24 can then be stimulated by the activatable light sources 32. The nonactivatable light sources 33 lying further away can remain switched off to save energy. The identification of the activatable light sources can be achieved by trial-based activation of individual light sources and by measurement of the response of the nerve cells 24. The measurement can be carried out via the electrodes 4 themselves or by means of a response measured in another way, for example by EEG, behavioral response, functional magnetic resonance imaging, PET, SPECT, pharmacological methods.

The invention claimed is:

1. An optical stimulation device for stimulating nerve cells, the stimulation device having at least one implant component configured for implantation in a natural inner cavity of the body of a living organism, through which cavity a body fluid flows, having the following features:
   a) the at least one implant component has at least one support structure which is expandable in a radial direction for fixation in the natural inner cavity,
   b) attached to the support structure is a multiplicity of light sources which are configured for radiation of light in the radial direction with respect to the at least one support structure,
   c) attached to the at least one support structure is a multiplicity of electrodes which are configured for capturing electric body signals,
   d) the at least one support structure has multiple openings and/or channels through which the body fluid can flow after implantation in the body, such that the light sources can be cooled by bathing the light sources in the body fluid.

2. The stimulation device as claimed in claim 1, wherein the implant component has a control electronics system and/or is connected via lines to a control electronics system arranged distantly from the implant component, wherein the control electronics system is configured for signal conditioning and/or signal processing of signals received via the electrodes and/or for activating the light sources.

3. The stimulation device as claimed in claim 2 wherein the control electronics system has a parameter memory in which an item of information is stored for each light source regarding whether the light source is activatable or not for the purposes of stimulation.

4. The stimulation device as claimed in claim 3 wherein the light sources are attached to the support structure in a predefined position with respect to the electrodes.

5. The stimulation device as claimed in claim 1 wherein the support structure has, in a nonexpanded state, a circumference of less than 10 mm.

6. The stimulation device as claimed in claim 1 wherein the support structure comprises a material having a high thermal conductivity.

7. The stimulation device as claimed in claim 1 wherein one or more light sources have thermally conductive heat sinks.

8. The stimulation device as claimed claim 1 wherein the implant component has a coupling element via which the implant component is coupleable to a flexible guide rod to be coupled to the implant component for carrying out the implantation process, the coupling of the coupling element to the flexible guide rod being disengageable by actuation of a release mechanism.

9. The stimulation device as claimed in claim 1 wherein at least some or all light sources are individually activatable.

10. The stimulation device as claimed claim 1 wherein the light sources and/or the electrodes are attached on a flexible support material which is attached to the support structure.

11. A method for programming the parameter memory of a stimulation device as claimed in claim 3, wherein the method is performed by the control electronics system, comprising the steps of:
   actuating all light sources for light emission,
   evaluating signals subsequently captured by means of the electrodes or signals captured by other nerve-signal capture methods,
   determining therefrom one or more individual light sources from the total multiplicity of light sources present that will be activatable in future,
   storing an identification of "activatable" in the parameter memory for these one or more individual light sources and
   storing the identification of "nonactivatable" for all other light sources of the multiplicity of light sources.

12. The simulation device as claimed in claim 5 wherein the circumference is less than 6 mm.

13. The simulation device as claimed in claim 6 wherein the thermal conductivity is greater than 10 W/m·K.

14. The simulation device as claimed in claim 7 wherein multiple light sources have thermally conductive heat sinks.

* * * * *